United States Patent [19]

Fountain et al.

[11] Patent Number: 5,000,958
[45] Date of Patent: Mar. 19, 1991

[54] ENHANCEMENT OF PHARMACEUTICAL ACTIVITY

[75] Inventors: Michael W. Fountain, Princeton; Steven J. Weiss, Hightstown; Robert P. Lenk, Lambertville; Mircea C. Popescu, Plainsboro; Richard S. Ginsberg, Monroe Township, Middlesex County, all of N.J.

[73] Assignee: The Liposome Company, Inc., Princeton, N.J.

[21] Appl. No.: 633,481

[22] Filed: Jul. 26, 1984

Related U.S. Application Data

[63] Continuation-in-part of Ser. No. 518,912, Aug. 1, 1983, abandoned.

[51] Int. Cl.$^5$ ............................................. A61K 37/22
[52] U.S. Cl. .................................... 424/450; 424/417
[58] Field of Search ................. 424/38, 19, 417, 450

[56] References Cited

U.S. PATENT DOCUMENTS

| | | | |
|---|---|---|---|
| 4,102,806 | 7/1978 | Kondo et al. | 424/38 |
| 4,235,871 | 11/1980 | Papahadjopoulo | 424/38 |
| 4,241,046 | 12/1980 | Papahadjopoulos | 424/19 |
| 4,328,222 | 5/1982 | Schmidt | 424/244 |
| 4,356,167 | 10/1982 | Kelly | 424/38 |
| 4,485,054 | 11/1984 | Mezei et al. | 264/4.6 |
| 4,588,578 | 5/1986 | Fountain et al. | 436/829 |

OTHER PUBLICATIONS

Goodwan and Gilman "The Pharmacological Bases of Therapeutics" 6th Edition, 1980 McMillan pp. 1097-1102.
Conn, Current Therapy, 1981 L. B. Saunders, pp. 10,23, 569.
Remingtons Pharmaceutical Science 15th Edition Mar. 1975 p. 1130.
Glew et al., Comparative Synergistic Activity of Nafcillin, Oxacillin, and Methicillin in Combination with Gentamicin Against Enterococci, Antimicrobial Agents and Chemotherapy 75, 828-32.

Primary Examiner—Stanley J. Friedman
Assistant Examiner—Kevin Weddington
Attorney, Agent, or Firm—Allen Bloom; Thomas S. Saunders; Ronald G. Ort

[57] ABSTRACT

The invention encompasses mixtures of antimicrobial agents coencapsulated in liposomes which when administered in vivo exert an enhanced therapeutic effect. The therapeutic effectiveness of the coencapsulated antimocrobial agents is greater than that of the same combination administered either in solution or as a mixture of liposome populations each containing one of the antimicrobial agents.

52 Claims, No Drawings

ENHANCEMENT OF PHARMACEUTICAL ACTIVITY

RELATED APPLICATIONS

This application is a continuation-in-part of U.S. Pat. application Ser. No. 518,912 filed Aug. 1, 1983, now abandoned.

TABLE OF CONTENTS

1. Introduction
2. Background of the Invention
    2.1. Therapy with Combined Antimicrobial Agents
    2.2. Liposomes and Uses of Liposome
3. Summary of the Invention
4. Description of the Invention
    4.1. Selection of Antimicrobial Agent
    4.2. The Liposome Preparations
    4.3. Therapeutic Uses of the Liposome Preparations
5. Example: Enhancement of Antibacterial Activity in Treating Salmonella typhimurium Infections SPLVs Containing Gentamycin and Nafcillin
    5.1. Preparation of SPLVs Containing Gentamycin or Nafcillin
    5.2. Preparation of SPLVs Containing Both Gentamycin and Nafcillin
    5.3. Treatment of Infected Mice
6. Example: Enhancement of Antibacterial Activity in Treating Salmonellosis Using SPLVs Containing Gentamycin and Nafcillin
    6.1. Preparation of SPLVs
    6.2 Infection of Mice Using Salmonella typhimurium
    6.3. Treatment of Infected Mice
7. Example: Enhancement of Antibacterial Activity in Treating Salmonella typhimurium Infections Using MPVs Containing Gentamycin and Nafcillin
    7.1. Preparation of MPVs Containing Both Gentamycin and Nafcillin
    7.2. Treatment of Infected Mice
Example: Enhancement of Antibacterial Activity in Treating Corynebacterium renale Pyelonephritis Using SPLVs Containing Gentamycin and Nafcillin
    8.1. Preparation of SPLVs
    8.2. Infection of Mice Using Corynebacterium renale
    8.3. Treatment of Infected Mice
9. Example: Enhancement of Antibacterial Activity in Treating Pseudomonas aeruginosa Pyelonephritis Using MPVs Containing Tobramycin and Ticarcillin
    9.1. Preparation of MPVs
    9.2. Infection of Rats Using Pseudomonas aeruginosa
    9.3. Treatment of Infected Rats
10. Enhancement of Antibacterial Activity Against Clostridium novyi Using SPLVs Containing Gentamycin and Clindamycin
    10.1. Preparation of SPLVs
    10.2 Infection of Mice Using Clostridium novyi
    10.3. Treatment of Infected Mice

1. INTRODUCTION

This invention relates to lipid vesicles incorporating certain mixtures of two or more antimicrobial agents which exert an enhanced therapeutic effect. This invention is based upon the discovery that in the treatment of infections in vivo (e.g., bacterial, fungal, viral, mycoplasmal, etc.), the therapeutic effectiveness of the combination of certain antimicrobial agents coencapsulated in one liposome preparation is greater than that obtained when the same combination of antimicrobial agents is administered either in solution or as a mixture of liposome preparations, each containing one of the antimicrobial agents. The coencapsulation of a number of combinations such as gentamycin (an aminoglycoside antibiotic) and nafcillin (a β-lactam antibiotic), or tobramycin (an aminoglycoside antibiotic) and ticarcillin (a β-lactam antibiotic), or gentamycin and clindamycin (a derivative of the amino acid trans-L-4-n-propylhygrinic acid, attached to a sulfur containing derivative of an octose) into one liposome preparation which is then used to treat infections in vivo is demonstrated herein by way of example.

2. BACKGROUND OF THE INVENTION

2.1. Therapy with Combined Antimicrobial Agents

Combinations of antimicrobial agents have been widely described for treatment of bacterial infections. The simultaneous administration of more than one antimicrobial agent has been suggested for several purposes: (1) to prevent or minimize the emergence of resistant mutants; (2) for the enhancement of therapeutic activity in the treatment of specific infections (for example, penicillin and certain aminoglycosides are recommended for the treatment of certain infections with gram negative bacteria); (3) to provide optimal therapy in severe infections for which the causative agent has not been clearly established (e.g., in the treatment of mixed bacterial infections); (4) to lessen the toxicity of individual drugs by reducing the dose of each in combination.

Certain combinations of antimicrobial agents demonstrate enhanced antimicrobial activity and clinical effectiveness in the treatment of some infections (see Table I).

TABLE I

ANTIMICROBIAL AGENTS USED IN THE THERAPY OF INFECTIONS[1]

| MICROORGANISM | DISEASE | DRUG COMBINATION |
| --- | --- | --- |
| Streptococcus viridans | Endocarditis Bacteremia | Penicillin G + streptomycin |
| Streptococcus agalactiae | Septicemia Meningitis | Ampicillin or penicillin G + an aminoglycoside |
| Group B Streptococcus faecalis (enterococcus) | Endocarditis Bacteremia | Penicillin G + an aminoglycoside |
| Corynebacterium sp. (diphtheroids) | Endocarditis | Penicillin G + an aminoglycoside |
| Listeria monocytogenes | Meningitis Bacteremia Endocarditis | Ampicillin + an aminoglycoside |
| Pseudomonas aeruginosa | Pneumonia Bacteremia | Carbenicillin or ticarcillin + gentamycin or tobramycin |
| Klebsiella pneumoniae | Pneumonia | A cephalosporin + gentamycin or tobramycin |
| Escherichia coli | Urinary tract infection | Ampicillin + gentamycin or trimethoprim-sulfamethoxazole |
| Shigella | Acute gastroenteritis | Trimethoprim-sulfamethoxazole |
| Yersinia enterocolitica | Yersiniosis | Trimethoprim-sulfamethoxazole |
| Pneumocystis carinii | Pneumonia in impaired hosts | Trimethoprim-sulfamethoxazole |
| Brucella | Brucellosis | A tetracycline + streptomycin |

TABLE I-continued
ANTIMICROBIAL AGENTS USED IN THE THERAPY OF INFECTIONS[1]

| MICROORGANISM | DISEASE | DRUG COMBINATION |
|---|---|---|
| Yersinia pestis | Plague | A tetracycline + streptomycin |
| Pseudomonas mallei | Glanders | A tetracycline + streptomycin |
| Pseudomonas pseudomallei | Melioidosis | A tetracycline + chloramphenicol |
| Mycobacterium tuberculosis | Pulmonary, miliary renal, meningeal and other tuberculosis infections | Isoniazid + ethambutol or rifampin |
| Mycobacterium leprae | Leprosy | Dapsone + rifampin |
| Chlamydia trachomatis | Trachoma | A sulfonamide + a tetracycline |
| Cryptococcus neoformuns | Meningitis | Amphotericin B + Flucytosine |
| Gram negative bacillary infections |  | Mecillinam + another β-lactam |

[1] From Goodman & Gilman, 1980, The Pharmacological Basis of Therapeutics, Sixth Edition, pp. 1080-1105.

The antimicrobial activity of antibiotics used in combinations may result in a supra-additive (synergistic) effect. For example, in the treatment of bacterial infections combinations such as penicillin or ampicillin and streptomycin or gentamycin have been shown to have a supra-additive effect against enterococci infections. Similarly, carbenicillin or ticarcillin combined with an aminoglycoside such as gentamycin or tobramycin exhibit a synergistic effect in the treatment of Pseudomonas aeruginosa infection. Combined therapy using streptomycin together with tetracycline is more effective in the therapy of brucellosis than either agent alone, and a mixture of chloramphenicol plus a sulfonamide is more effective against meningitis due to Hemophilus influenzae.

The utility of combinations of drugs in the antimicrobial therapy of fungal infections has also been recognized. The concurrent administration of low doses of amphotericin B (20 mg daily) and flucytosine (150 mg/kg per day) for 6 weeks appears to be superior to using either drug alone in treating cryptococcosis as measured by a more rapid rate of sterilization of cerebrospinal fluid, reduced toxicity, and increased overall rate of cure. In addition, primary amebic meningoencephalitis has responded to a combination of miconazole, rifampin and intrathecal amphotericin B. Combinations of amphotericin B with other agents including flucytosine, rifampin, or tetracycline have been found to enhance antifungal activity.

Similarly the use of combinations of antiviral agents is currently being explored. Recently, the combination of acyclovir and vidarabine was reported to be more effective than the individual drugs in diminishing the development of clinical signs of herpes simplex virus type 1 infection in hairless mice (Park, et.al., 1984, The Journal of Infectious Diseases 149(5): 757-762).

However, combinations of drugs may be antagonistic rather this synergistic. For instance, the addition of a bacteriostatic drug (tetracycline) to a bactericidal drug (penicillin) produces a decrease in activity since penicillins can act only against microorganisms that are multiplying. Thus, a number of in vitro assays are used to predict the potential therapeutic efficacy of combinations of antibiotics. These assays quantitate the effects of the antibiotics on bacterial growth in vitro.

One method, which is used to predict the efficacy of antibacterial agents is described by Scribner et.al., (1982, Antimicrobial Agents and Chemotherapy 21(6):939-943) and in Goodman & Gilman (1980, The Pharmacological Basis of Therapeutics, Sixth Edition, pp. 1097-1098) and is referred to as the checkerboard assay. This assay involves serial two-fold dilutions of the antibiotics individually and in combination in broth which is then inoculated with the microorganism to be tested. After incubation, the minimum inhibitory concentration (MIC) of each drug used individually and in combination is determined (N.B., the MIC is the lowest concentration of the drug that inhibits growth in the medium). Synergism is indicated by a decrease in the MIC of each drug when used in combination. Antagonism is indicated by an increase in the MIC of either or both drugs when used in combination. This assay is described in more detail infra and is used in the present invention to determine whether certain combinations of antimicrobial agents (e.g., antibacterial or antifungal) are non-antagonistic.

Another method for the evaluation of drug combinations involves quantifying the rate of bacteriocidal action. Identical cultures are incubated with antibiotics added singly or in combination. Synergism is indicated if a combination of antibiotics is more rapidly bacteriocidal then either drug alone.

Similarly, combinations of antiviral agents may be assayed in vitro and classified as synergistic, additive, antagonistic, etc. Such an assay is described by Park et.al., 1984, The Journal of Infectious Diseases 149(5): 757-762. Briefly, the assay involves infection of confluent host cells in vitro with virus and treatment of the infected cells with various concentrations of the antiviral agents individually and in combination. After incubation, the virus titers recovered from the treated cells are determined by comparing the degree of titer reduction obtained when each drug is used singly to the degree of titer reduction obtained when the drugs are used in combination. This assay is also described in more detail infra and is used in the present invention to determine whether certain combinations of antiviral drugs are non-antagonistic.

In many instances, concurrent therapy with certain antimicrobial agents is further complicated because agents which exert a synergistic effect in vitro cannot be formulated in a single mixture for use in vivo. Mixtures of gentamycin and nafcillin at therapeutically effective concentrations result in the formation of complexes that precipitate out of solution and, therefore, are not administered in vivo. In fact, certain drug combinations are not recommended for use in vivo due to drug incompatibility (i.e., either inactivation of the drug or formation of a precipitate). For example, it is recommended that the following antibiotics not be mixed with any other drug: gentamycin, kanamycin, lincomycin, cephalothin, and ampicillin (Davis and Abbitt, 1977, JAVMA 170(2): 204-207). Finally, certain agents cannot be solubilized in the same media due to chemical restraints (e.g., a lipid soluble compound and a water soluble compound). These limitations reduce the possible combinations of agents that may be used to obtain enhancement of biological activity in combined therapy. For a review of the topic see Goodman and Gilman, 1980, *The Pharmacological Basis of Therapeutics*

Sixth Edition, pp. 1080–1106 and 1239–1240 and Davis et.al., 1980, *Microbiology*, pp. 574–583.

2.2. Liposomes and Uses of Liposomes

Liposomes are closed bilayer membranes containing an entrapped aqueous volume. Liposomes may be any variety of unilamellar vesicles (possessing a single membrane bilayer) or multilamellar vesicles (onion-like structures characterized by concentric lipid bilayers each separated from the next by an aqueous layer).

The original liposome preparation of Bangnam et. al., (1965, J. Mol. Biol. 13:238–252) involves suspending phospholipids in an organic solvent which is then evaporated to dryness leaving a waxy deposit of phospholipid on the reaction vessel. Then an appropriate amount of aqueous phase is added, the mixture is allowed to "swell", and the resulting liposomes which consist of multilamellar vesicles (hereinafter referred to as MLVs) are dispersed by mechanical means. The structure of the resulting membrane bilayer is such that the hydrophobic (non-polar) "tails" of the lipid orient toward the center of the bilayer while the hydrophilic (polar) "heads" orient towards the aqueous phase. This technique provided the basis for the development of the small sonicated unilamellar vesicles (hereinafter referred to as SUVs) described by Papahadjapoulos and Miller (1967, Biochim. Biophys. Acta. 135:624–638). These "classical liposome" preparations have a number of disadvantages however, including the wide heterogeneity in size distribution, the number of lamellae, and the low trapping efficiency of the aqueous space which restrict the ability to encapsulate large molecules.

Efforts to increase the entrapped volume involved first forming inverse micelles or liposome precursors, i.e., vesicles containing an aqueous phase surrounded by a monolayer of lipid molecules oriented so that the polar head groups are directed towards the aqueous phase. Liposome precursors are formed by adding the aqueous solution to be entrapped to a solution of polar lipid in an organic solvent and sonicating. The solvent is evaporated in the presence of excess lipid. The resultant liposomes, consisting of an aqueous phase entrapped by a lipid bilayer are dispersed in the aqueous phase (see U.S. Pat. No. 4,224,179 issued Sept. 23, 1980 to M. Schneider).

In another attempt to maximize the efficiency of entrapment, Papahadjapoulos (U.S. Pat. No. 4,235,871 issued Nov. 25, 1980) describes a "reverse-phase evaporation process" for making oligolamellar lipid vesicles also known as reverse-phase evaporation vesicles (hereinafter referred to as REVs). According to this procedure, the aqueous material to be entrapped is added to a mixture of polar lipid in an organic solvent. Then a homogeneous water-in-oil type of emulsion is formed and the organic solvent is evaporated until a gel is formed. The gel is then converted to a suspension by dispersing the gel-like mixture in an aqueous media. The REVs produced consist mostly of unilamellar vesicles and some oligolamellar vesicles which are characterized by only a few concentric bilayers with a large internal aqueous space. Certain permeability properties of REVs were reported to be similar to those of MLVs and SUVs (see Szoka and Papahadjapoulos, 1978, Proc. Natl. Acad. Sci. U.S.A. 75:4194–4198).

Although liposomes which entrap a variety of substances can be prepared, the stability of the liposomes during storage may be limited. This loss in stability results in leakage of the entrapped compound from the liposomes into the surrounding media, and can also result in contamination of the liposome contents by permeation of materials from the surrounding media into the liposome itself. As a result the storage life of traditional liposomes is very limited. Attempts to improve stability involved incorporating certain substances (hereinafter called "stabilizers") which affect the physical properties of the lipid bilayers (e.g., sterols) into the lipid membrane.

Much has been written regarding the potential use of liposomes as drug delivery systems although a number of problems with such systems exist (e.g., rapid clearance of the liposomes in vivo, instability of the liposomes, etc.) In a liposome drug delivery system the medicament is entrapped during liposome formation and then administered to the patient to be treated. Typical of such disclosures are U.S. Pat. No. 3,993,754 issued on Nov. 23, 1976 to Rahman and Cerny, and U.S. Pat. No. 4,145,410 issued on Mar. 20, 1979 to Sears. U.S. Pat. 4,235,871 issued Nov. 25, 1980 to Papahadjapoulos and Szoka and U.S. Pat. 4,224,179 issued Sept. 23, 1980 to Schneider, U.S. Pat. 4,356,167 issued Oct. 26, 1982 to L. Kelly, and U.S. Pat. 4,377,567 issued Sept. 13, 1979 to Geho.

An improved method for the chemotherapy of leishmanial infections using a liposome encapsulated antileishmanial drug has been reported by Steck and Alving in U.S. Pat. No. 4,186,183 issued on Jan. 29, 1980.

3. SUMMARY OF THE INVENTION

The present invention relates to liposome preparations in which two or more non-antagonistic antimicrobial agents are coencapsulated in one liposome preparation. The liposome preparation may be administered in a single dose in vivo to obtain a greatly enhanced therapeutic effect. The therapeutic effectiveness of the antimicrobial agents coencapsulated in liposomes is greater than that of the same combination of antimicrobial agents administered either in solution or as a mixture of liposome preparations each containing one of the antimicrobial agents. The combinations of antimicrobial agents which may be coencapsulated are determined by testing the unencapsulated combination in the assays described below which are referred to as the Combination Effect Test. The liposomes are prepared by the addition of each antimicrobial agent to the liposome ingredients prior to or during formation of the liposomes. The practice of the present invention is demonstrated herein using combinations such as gentamycin and nafcillin or tobramycin and ticarcillin, or clindamycin and gentamycin coencapsulated in one stable liposome preparation to treat various infections in vivo such as Salmonellosis, Corynebacterium Pyelonephritis, Pseudomonas Pyelonephritis, and Clostridium wound infections.

The invention includes a method for the treatment of an infection by administering to an organism a liposome-drug preparation comprising at least two non-antagonistic antimicrobial agents coencapsulated in lipid vesicles, the agent being synergistic in unencapsulated form. This further includes agents where synergy is determined by the Combination Effect Test (infra). This yet further includes agent demonstrating addition as determined by the Combination Effect Test. This still further includes at least on of the antimicrobial agents being antibacterial.

The invention additionally includes a method for the treatment of an infection by administering to an organism a liposome-drug preparation comprising at least two non-antagonistic antimicrobial agents coencapsulated in lipid vesicles in which the antimicrobial agents demonstrate indifference in their unencapsulated form as determined by the Combination Effect Test.

The invention further includes a method for the treatment of an infection by administering to an organism a liposome-drug preparation comprising at least two antimicrobial agents coencapsulated in lipid vesicles in which the therapeutic index (infra) of the liposome-drug preparation is greater than the index of the combined antimicrobial agents in their unencapsulated form, particularly where at least one antimicrobial agent is antibacterial.

The invention also includes a method for the treatment of an infection by administering to an infected organism a liposome-drug preparation of stable plurilamellar vesicles including either gentamycin and nafcillin or tobramycin and ticarcillin or gentamycin and clindamycin. The invention includes using this method for treating Salmonella spp., Pseudomonas spp. and Clostridium spp., particularly by parenteral administration.

The invention additionally includes a method for the treatment of an infection by a microbial agent by administering to the infected organism an effective amount of a liposome-drug preparation of monophasic vesicles and either gentamycin and nafcillin or tobramycin and ticarcillin or gentamycin and clindamycin. The invention includes using this method for treating Salmonella spp., Pseudomonas spp. and Clostridium spp., particularly by parenteral administration.

4. DESCRIPTION OF THE INVENTION

The present invention involves liposome preparations incorporating combinations of antimicrobial agents and their use. Non-antagonistic antimicrobial agents are coencapsulated, i.e., entrapped within the aqueous compartment and/or inserted in the membrane bilayer, in a single liposome preparation. When the liposome preparation is administered in vivo, a greatly enhanced therapeutic effect is obtained. This invention enables concomitant administration of combinations of certain drugs in vivo.

4.1. Selection of Antimicrobial Agents

According to one embodiment of the present invention, combinations of antimicrobial agents which exert a supra-additive effect or synergistic effect are encapsulated in one liposome preparation (hereinafter referred to as coencapsulation which is further defined in Section 4.2.). A number of combinations of antimicrobial agents which are known to be synergistic may be encapsulated in one liposome preparation; examples of these combinations include but are not limited to those listed in Table I and in Section 2.1. supra.

Additional combinations of antimicrobial agents may be selected based upon the in vitro assays previously described in Section 2.1 which are used to determine the effectiveness of a combination of antimicrobial agents. These assays include (1) the Checkerboard Assay, which as defined herein may be used to evaluate the effectiveness of combinations against bacteria or fungi; and (2) the virus titer reduction assay. These in vitro assays, described in detail below, will hereinafter be collectively referred to as the Combination Effect Test:

(A) The Checkerboard Assay. Serial dilutions (usually two-fold) of the antimicrobial agents are made in a checkerboard fashion so that a large number of antimicrobial concentrations in different proportions can be tested simultaneously. The checkerboard consists of horizontal rows which contain the same amount of drug A diluted along the X-axis, and vertical rows which contain the same amount of drug B diluted along the Y-axis. Thus, for a given range of dilutions, every possible combination of both drugs is achieved. The technique may be performed in broth or agar containing the nutrients necessary to support the growth of the test microorganism (e.g., bacteria, fungus, and the like). Then a standard inoculum of the test microorganism is added to each dilution and the cultures are incubated under appropriate conditions and examined for growth. The minimal inhibitory concentration (MIC), i.e., the greatest dilution of each test solution which inhibits growth of the microorganism, is determined for each antimicrobial agent and the combination. The combination effects are defined by Scribner et.al. (supra) as follows: (1) synergy is indicated by at least a fourfold reduction in the MIC of each antibiotic; (2) addition is indicated by a twofold reduction in the MIC of either or both antibiotics; (3) indifference is indicated by no change in the MIC of the antibiotics; and (4) antagonism is indicated by a fourfold increase in the MIC of either or both antibiotics.

(B) The Virus Titer Reduction Assay. Confluent host cells in vitro are infected with the virus of interest. After washing the cells, media containing various concentrations of antiviral agents individually and in combination are added in duplicate to the appropriate cell cultures. After incubation under appropriate conditions the virus is recovered from the cell cultures and virus titers are assays, e.g., using an ordinary plaque assay. The combined effects of the antiviral agents in culture are determined by the following criteria (as reported by Park et.al., 1984, supra): (1 $E_A$ (effect of drug A)=titer of virus produced in the presence of drug A/titer of virus produced in the absence of drug. (2) $E_B$ (effect of drug B)=titer of virus produced in the presence of drug B/titer of virus produced in the absence of drug. (3) $E_{AB}$ (effect of the combination of drugs A and B)=titer of virus produced in the presence of drugs A and B/titer of virus produced in the absence of drug. (4) $E_C$ (calculated effect of combined drugs A and B, or additive effect of drugs A and B)=$E_A \times E_B$. A synergistic interaction of the drugs can be defined as $E_{AB} < E_C$ and an additive effect as $E_{AB} = E_C$. Moreover, if drug A is assumed to be more effective than drug B, an less-than-additive (subadditive) interaction of the combined drugs is defined as $E_C < E_{AB} < E_A$; an antagonistic interaction as $E_B < E_{AB}$; and interference as $E_A < E_{AB} < E_B$.

Accordingly, those unencapsulated combinations that prove to be non-antagonistic (i.e., those that are synergistic, additive, subadditive or indifferent) based upon the Combination Effect Test may be coencapsulated in one liposome preparation in accordance with the present invention.

Aside from the criteria established in vitro in the Combination Effect Test described above, any combination of antimicrobial agents which when coencapsulated in one liposome preparation demonstrate an increased therapeutic index as compared to that of the unencapsulated antimicrobial agents is also contemplated as being within the scope of the present invention. The therapeutic index refers to the dose ratio between toxic and therapeutic effects. The therapeutic index in animals can be expressed as the ratio, LD50/ED50, wherein LD50 is the dose lethal to 50% of a population and ED50 is the dose therapeutically effective in 50% of a comparable population. Therefore, the greater the therapeutic index, the greater the safety margin for a particular drug.

Combinations of antimicrobial agents including but not limited to the following may be coencapsulated into one liposome preparation: the combinations of antimicrobial agents listed in Table I and in section 2.1; erythromycin + an aminoglycoside; ampicillin + streptomycin; gentamycin + carbenicillin; gentamycin + nafcillin; chloramphenicol + streptomycin; isoniazid + ethambutol; isoniazid + ethambutol + streptomycin; a sulfonamide + a tetracycline; amphotericin B + flucytosine; a sulfonamide + streptomycin; a sulfonamide + ampicillin; a tetracycline + cycloserine; a penicillin or ampicillin and gentamycin or tobramycin; steroids with water soluble or lipid soluble antibiotics; and acyclovir and vidarabine.

4.2. The Liposome Preparations

According to the present invention, a combination of antimicrobial agents is encapsulated in a liposome preparation by the addition of each agent to the liposome ingredients prior to or during formation of the lipid vesicles. Thus, two or more antimicrobial agents are added to either the aqueous phase or the organic phase during the formation of the liposomes so that each, according to its solubility, is incorporated into the liposome bilayer or the aqueous phase of the resultant liposome (i.e., coencapsulation).

The method used to prepare the liposomes depends upon both the type of liposomes to be used and the nature of the antimicrobial agents to be encapsulated. Stable liposomes are preferred as are liposomes which entrap a high percentage of drug.

A particularly suitable liposome preparation which may be used in the practice of the present invention are SPLVs (stable plurilamellar vesicles). SPLVs are described in U.S. Pat. application Ser. No. 476,496, filed Mar. 24, 1983, which is incorporated by reference herein.

SPLVs are prepared as follows: An amphipathic lipid or mixture of lipids is dissolved in an organic solvent. Many organic solvents are suitable, but diethyl ether, fluorinated hydrocarbons and mixtures of fluorinated hydrocarbons and ether are preferred. To this solution are added an aqueous phase and the active ingredients to be entrapped. This biphasic mixture is converted to SPLVs by emulsifying the aqueous material within the solvent and evaporating the solvent. Evaporation can be accomplished during or after sonication by any evaporative technique, e.g., evaporation by passing a stream of inert gas over the mixture, by heating, or by vacuum. The volume of solvent used must exceed the aqueous volume by a sufficient amount so that the aqueous material can be completely emulsified in the mixture. In practice, a minimum of roughly 3 volumes of solvent to 1 volume of aqueous phase may be used. In fact the ratio of solvent to aqueous phase can vary to up to 100 or more volumes of solvent to 1 volume aqueous phase. The amount of lipid must be sufficient so as to exceed that amount needed to coat the emulsion droplets (about 40 mg of lipid per ml of aqueous phase). The upper boundary is limited only by the practicality of cost-effectiveness, but SPLVs can be made with 15 gm of lipid per ml of aqueous phase.

Thus, a lipid-soluble antimicrobial agent may be added directly to the organic phase of the liposome ingredients which ultimately forms the liposome bilayer. A water-soluble antimicrobial agent may be added to the aqueous phase prior to bilayer formation and entrapment. In fact, a lipid soluble agent added with the aqueous phase will partition into the lipid component of the resultant vesicles.

If the combination of antimicrobial agents in solution forms a precipitate complex, i.e., if the agents are incompatible, then a solution of each agent is added to the liposome ingredients simultaneously but separately in order to avoid precipitation.

Another suitable liposome preparation which may be used in the practice of the present invention is lipid vesicles prepared in a monophasic solvent system, hereinafter referred to as monophasic vesicles or MPVs. MPVs are described in U.S. Pat. application Ser. No. 521,176, filed Aug. 8, 1983, which is incorporated by reference herein. MPVs are particularly stable and have a high entrapment efficiency. MPVs are prepared as follows: an amphipathic lipid or mixture of lipids is dissolved in an organic solvent which is also miscible with water (hereinafter referred to as a monophasic solvent) such as an alcohol (e.g. ethanol). If an antimicrobial agent to be entrapped is lipid soluble, this agent is directly added to the lipid monophasic solution; if an antimicrobial agent to be entrapped is water soluble then this agent is added in a small volume of aqueous solution (e.g., 0.1–0.3 ml aqueous to 10 ml ethanol containing 100 mg lipid). As previously explained, if the combination of antimicrobial agents in solution forms a precipitate complex, i.e., if the agents are incompatible, then a solution of each agent is added to the monophasic solvent-lipid solution simultaneously but separately in order to avoid precipitation. The resulting mixture is a total dispersion (no biphase results). The solution is then evaporated at a temperature dependent upon the boiling point of the monophasic solvent (e.g. a range of 40° C. to 100° C.) for a few minutes until a clear film (comprising the lipid and bioactive agents) forms on the side walls of the vessel. Then a small volume of aqueous solution is added, the mixture is resuspended and agitated in order to form the MPVs containing the entrapped bioactive agents.

Besides increased stability and a higher percentage of entrapment, SPLVs and MPVs offer other advantages over conventional MLVs when used in the practice of the present invention. For example, chemically incompatible agents such as gentamycin and nafcillin can be effectively put in SPLVs and MPVs, but not in MLVs without first diluting the drugs; such dilution reduces the amount of drug entrapped and, therefore, increases the volume necessary to deliver the effective dose.

4.3. Therapeutic Uses of the Liposome Preparations

The enhancement of antimicrobial activity in the treatment of specific infections can be achieved by the administration in vivo of the combination of non-antagonistic antimicrobial agents coencapsulated in one liposome preparation. When administered to an animal, the liposome preparations described herein exert enhanced biological activity and clinical effectiveness.

The liposome preparations described herein offer a particular advantage in situations where conventional combined drug therapy is unsuccessful or marginally useful. For instance, the drugs isoniazid, rifampin, ethambutol, and streptomycin have been successfully used in various combinations in the treatment of tuberculosis. However, during therapy multiply resistant tubercle bacilli may appear, possibly due to the unequal distribution of the drug in the body simultaneously. Liposome coencapsulated drug combinations provide a means for maintaining the effective concentration of the drugs in the body simultaneously.

The liposome preparations described herein also offer an advantage over combined therapy using two chemotherapeutic agents which normally exert a synergistic or supra-additive effect (previously described). If the two agents are present in a single liposome, they are more effective as antimicrobial agents in combined therapy than if presented separately. This enhanced effect is probably due to the fact that both agents are available at the site of infection at the same time. In fact, treatment of infections with multiple synergistic drugs coencapsulated in one liposome preparation is therapeutically more effective than treatment using the same drugs encapsulated in separate liposome preparations which are mixed together prior to administration in vivo.

The liposome preparations described herein offer an advantage in the treatment of intracellular infections and may offer an advantage in the treatment of extracellular infections. The coencapsulation of multiple drugs in a single liposome preparation administered in vivo increases the probability that the particular drugs are directed to a specific site (either intracellular or extracellular), thus enhancing their biological action and/or therapeutic effect.

When treating an intracellular infection, the liposome preparations containing the drug combinations described herein may be administered parenterally. The liposome-encapsulated drugs may be delivered to the site of infection when the infected cells endocytose the liposomes. Endocytosed liposomes appear in the cellular digestive apparatus, the phagolysosomes. The degree of endocytosis depends on the type of liposomes and the target cells. Once the liposome is internalized, the combination of drugs which were coencapsulated probably become available to combat the infection in the cell.

The liposome preparations described herein may be used to treat extracellular infections in vivo. Accordingly, parenteral administration of liposomes containing coencapsulated multiple drugs delivers the therapeutic substances to the highly phagocytic macrophages of the reticuloendothelial system. The macrophages coalesce with the liposomes and become "loaded" with the liposome-encapsulated agents. Once the "loaded" macrophages reach the site of infection (e.g., a systemic extracellular infection), the macrophages will engulf the pathogen; as a result, the pathogen will come in contact with the combination of drugs in the macrophage and be destroyed.

The following examples are given for the purpose of illustration and are not by way of limitation on the scope of the invention.

5. EXAMPLE: ENHANCEMENT OF ANTIBACTERIAL ACTIVITY IN TREATING *SALMONELLA TYPHIMURIUM* INFECTIONS USING SPLVs CONTAINING GENTAMYCIN

In the following example, the antibacterial activity of various preparations of the aminoglycoside, gentamycin, and the penicillinase-resistant penicillin, nafcillin, are compared. The results demonstrate that of the preparations tested, treatment of lethal infections of *Salmonella typhimurium* (an intracellular infection) in mice is most effective using an SPLV preparation in which both gentamycin and nafcillin are incorporated into one SPLV preparation.

5.1. Preparation of SPLVs Containing Gentamycin or Nafcillin

A 5 ml diethyl ether solution of 100 mg egg phosphatidyl choline (EPC, or egg lecithin) was prepared. The mixture was placed in a round bottom flask. Then a solution (0.3 ml) containing 200 mg of gentamycin or nafcillin in phosphate buffered saline (PBS, pH 7.2) was pipetted into the flask containing the diethyl ether solution of lipid. The mixture was placed in a bath sonicator (Laboratory Supplies Co., Inc., type 10536) for several minutes (80 kHz frequency; output 80 watts) while being dried to a viscous paste by passing a gentle stream of nitrogen over the mixture.

To the viscous part remaining, 10 ml of PBS was added. The resulting SPLV preparation containing either nafcillin (SPLV/Naf) or gentamycin (SPLV/Gent) was suspended in PBS, shaken and freed of nonencapsulated antibiotic by centrifugation at $12,000 \times g$ for 10 minutes at 20° C. The resulting pellet was washed one more time and resuspended in 0.5 ml PBS.

5.2. Preparation of SPLVs Containing Both Gentamycin and Nafcillin

In order to prepare SPLVs containing both nafcillin and gentamycin, the procedure described above was followed with the following modifications: after the EPC was dispersed in diethyl ether, two solutions, one of each antibiotic, were added quickly and simultaneously, each solution consisted of 100 mg antibiotic (nafcillin or gentamycin) dissolved in 0.15 ml PBS. After the addition of the two solutions, the preparation was sonicated, evaporated, and washed two times as previously described. The resulting SPLVs entrapped both gentamycin and nafcillin (SPLV/Gent-Naf).

5.3. Treatment of Infected Mice

One hundred twenty-fice mice were infected by intraperitional (I.P.) inoculation of a lethal dose (i.e., $3 \times 10^6$ colony forming units, CFU) of *Salmonella typhimurium* in order to establish septicemia. Twenty-four hours after inoculation the mice were divided into 8 groups of mice and each was treated as follows: Group 1 (controls) received no treatment; Group 2 received aqueous nafcillin (100 mg/kg body weight, I.P.); Group 3 received aqueous gentamycin (100 mg/kg body weight, I.P.); Group 4 received a single preparation containing both aqueous gentamycin (50 mg/kg body weight, I.P.) and nafcillin (50 mg/kg body weight, I.P.);Group 5 received SPLVs containing nafcillin (100 mg antibiotic/kg body weight, I.P.); Group 6 received SPLVs containing gentamycin (100 mg antibiotic/kg body weight); Group 7 received a mixture of two SPLV preparations, one containing gentamycin (50 mg/kg body weight, I.P.) and the other SPLV preparation containing nafcillin (50 mg/kg body weight, I.P.) prepared as described in Section 5.1.; and Group 8 received one SPLV preparation containing both gentamycin (50 mg/kg body weight, I.P.) and nafcillin (50 mg/kg body weight, I.P.) prepared as described in Section 5.2. Results are shown in Table II.

The results shown in Table II clearly indicate that the SPLVs containing both gentamycin and nafcillin were most effective in preventing mortality due to infection. In fact, the administration of the SPLV preparation containing both gentamycin and nafcillin was not only more effective in preventing mortality than was the administration of both drugs in an aqueous solution, but surprisingly treatment with the SPLV preparation containing both gentamycin and nafcillin was more effective in preventing mortality than was the simultaneous treatment with two populations of SPLVs, one containing gentamycin and the other containing nafcillin.

6. EXAMPLE: ENHANCEMENT OF ANTIBACTERIAL ACTIVITY IN TREATING SALMONELLOSIS USING SPLVs CONTAINING GENTAMYCIN AND NAFCILLIN

In this example, the antibacterial activity and clinical effectiveness of SPLVs containing both gentamycin and nafcillin are compared to a number of other preparations. The results indicate that of the preparations tested, treatment of *Salmonella typhimurium* is most effective when using an SPLV preparation in which gentamycin and nafcillin are both incorporated into one liposome preparation.

ml using physiological saline; (b) SPLVs containing both nafcillin and gentamycin (SPLV/NAF-GENT) in one liposome preparation were suspended to a total volume of 2 ml using physiological saline; (c) SPLVs containing nafcillin were suspended to a total volume of 1 ml using physiological saline. A 0.5 ml aliquot of this suspension was resuspended to a final volume of 1 ml using physiological saline to which 20 mg gentamycin was added (SPLV/NAF in gentamycin, aq.); (d) SPLVs containing gentamycin were suspended to a total volume of 1 ml. A 0.5 ml aliquot of this suspension was resuspended to a final volume of 1 ml using physiological saline to which 20 mg nafcillin was added (SPLV/GENT in nafcillin, aq.); (e) the remaining 0.5 ml aliquot of SPLVs containing nafcillin in physiologic saline (see (c) above) was added to a 0.5 ml aliquot of SPLVs containing gentamycin in physiologic saline (SPLV/NAF and SPLV/GENT). The resuspended SPLV preparations had the following compositions per 0.1 ml aliquot: (a) SPLVs=20 mg EPC; (b) SPLV/NAF-GENT=20 mg EPC, 2 mg nafcillin, 2 mg gentamycin; (c)SPLV/NAF in gentamycin, aq.=20 mg EPC, 2 mg nafcillin, 2 mg gentamycin; (d) SPLV/GENT in nafcillin, aq.=20 mg EPC, 2 mg gentamycin, 2 mg nafcillin; and (e) SPLV/NAF and SPLV/GENT=40 mg EPC, 2 mg nafcillin, 2 mg gentamycin.

TABLE II
ENHANCED EFFECT OF SPLV-ENTRAPPED GENTAMYCIN AND NAFCILLIN

| GROUP[a] | SURVIVAL DAYS AFTER INFECTION DAYS POST TREATMENT | | | | | | | | % SURVIVAL |
|---|---|---|---|---|---|---|---|---|---|
| | 1 | 2 | 3 | 4 | 5 | 6 | 7 | 8 | 14 | |
| GROUP 1 CONTROL (untreated) | | | 4/25 | 0/25 | 0/25 | 0/25 | 0/25 | 0/25 | 0/25 | 0 |
| GROUP 2 NAFCILLIN (aq.) | | | 0/15 | 0/15 | 0/15 | 0/15 | 0/15 | 0/15 | 0/15 | 0 |
| GROUP 3 GENTAMYCIN (aq.) | 2/15[c] | 0/15 | 0/15 | 0/15 | 0/15 | 0/15 | 0/15 | 0/15 | 0/15 | 0 |
| GROUP 4 GENT/NAF (aq.) | | 9/10 | 5/10 | 1/10 | 0/10 | 0/10 | 0/10 | 0/10 | 0/10 | 0 |
| GROUP 5 SPLV/ NAFCILLIN | | | | 1/15 | 1/15 | 1/15 | 1/15 | 0/15 | 0/15 | 0 |
| GROUP 6 SPLV/ GENTAMYCIN | | | | 1/15 | 1/15 | 1/15 | 1/15 | 0/15 | 0/15 | 0 |
| GROUP 7 SPLV/ NAFCILLIN AND SPLV/ GENTAMYCIN | | | | 1/15 | 1/15 | 1/15 | 1/15 | 0/15 | 0/15 | 0 |
| GROUP 8 SPLV/ GENT-NAF | | | | 15/15 | 15/15 | 15/15 | 15/15 | 14/15 | 14/15 | 93.3 |

[a]Each group of mice received a total of 100 mg antibiotic/kg body weight (except for the control group which received no treatment) 24 hours after infection with a lethal dose of *S. typhimurium* (3 × 10⁶ CFU, I.P.).
[b]Survival is expressed as the number of mice alive divided by the total number of mice in the group.
[c]These mice died immediately after injection of gentamycin due to acute toxicity of the gentamycin.

6.1. Preparation of SPLVS

SPLVs containing no drug and SPLVs containing either gentamycin or nafcillin, were prepared as described in Section 5.1 using 200 mg EPC and 200 mg of drug. SPLVs containing both gentamycin and nafcillin were prepared as described in Section 5.2 using 200 mg EPC and 200 mg of each drug.

Each SPLV preparation was washed four times and resuspended in the following solutions: (a) SPLVs containing no drug were suspended to a total volume of 2

6.2. Infection of Mice Using Salmonella Typhimurium

Hilltop mice (20–30 mg each) were infected with *Salmonella typhimurium* by intraperitoneal injection of 0.3 ml of a culture of *S. typhimurium* in BHI broth (Brain Heart Infusion Media, BBL Microbiological Systems, Cockeysville, Md.) grown to an $O.D._{420}$ of about 0.18.

6.3. Treatment of Infected Mice

Twenty seven hours after infection with *S. typhimurium* the mice were divided into 7 groups and each group was treated by inoculation of 0.1 ml (either I.P. or I.V., intravenous) as follows: Group 1 (controls) were untreated; Group 2 received SPLVs containing no drug (I.V.); Group 3 received SPLV/GENT in nafcillin, aq. (100 mg of each antibiotic/kg body weight, I.V.); Group 4 received SPLV/NAF in gentamycin, aq. (100 mg of each antibiotic/kg body weight, I.V.); Group 5 received a mixture of two liposome populations, SPLV/NAF and SPLV/GENT (100 mg of each antibiotic/kg body weight, I.V.); Group 6 received SPLV/NAF-GENT (100 mg of each antibiotic/kg body weight, I.V.); and Group 7 received SPLV/NAF-GENT (100 mg of each antibiotic per kg body weight, I.P.). Results are shown in Table III.

TABLE III

EFFECT ON SPLV ENTRAPPED GENTAMYCIN AND NAFCILLIN ON SALMONELLA TYPHIMURIUM INFECTION IN MICE

| GROUP | SURVIVAL DAYS AFTER TREATMENT | | | | | | | | | % Survival |
|---|---|---|---|---|---|---|---|---|---|---|
| | 1-3 | 4-5 | 6 | 7 | 8 | 9 | 10 | 11-12 | 13 | |
| GROUP 1 CONTROL (untreated) | 5/5 | 3/5 | 2/5 | 1/5 | 1/5 | 1/5 | 1/5 | 0/5 | 0/5 | 0 |
| GROUP 2 SPLVS (I.V.) | 5/5 | 3/5 | 3/5 | 1/5 | 0/5 | 0/5 | 0/5 | 0/5 | 0/5 | 0 |
| GROUP 3 SPLV/GENT IN NAFCILLIN, aq. (I.V.) | 5/5 | 3/5 | 3/5 | 3/5 | 2/5 | 2/5 | 2/5 | 1/5 | 1/5 | 20 |
| GROUP 4 SPLV/NAF IN GENTAMYCIN aq. (I.V.) | 5/5 | 4/5 | 4/5 | 0/5 | 0/5 | 0/5 | 0/5 | 0/5 | 0/5 | 0 |
| GROUP 5 SPLV/NAF AND SPLV/GENT (I.V.) | 5/5 | 4/5 | 4/5 | 3/5 | 3/5 | 3/5 | 1/5 | 1/5 | 0/5 | 0 |
| GROUP 6 SPLV/ NAF-GENT (I.V.) | 5/5 | 5/5 | 5/5 | 5/5 | 5/5 | 4/5 | 4/5 | 4/5 | 4/5 | 80 |
| GROUP 7 SPLV/ NAF-GENT (I.P.) | 5/5 | 5/5 | 4/5 | 4/5 | 4/5 | 3/5 | 3/5 | 3/5 | 3/5 | 60 |

These results demonstrate the increased effectiveness of the combination of nafcillin and gentamycin entrapped in one liposome preparation in the treatment of *S. typhimurium* infection in vivo whether administered intravenously or intraperitoneally.

7 EXAMPLE: ENHANCEMENT OF ANTIBACTERIAL ACTIVITY IN TREATING *SALMONELLA TYPHIMURIUM* INFECTIONS USING MPVs CONTAINING GENTAMYCIN AND NAFCILLIN

In this example, the antibacterial activity and clinical effectiveness of various preparations of the antibiotics gentamycin and penicillin are compared. The results indicate that of the preparations tested, treatment of *S. typhimurium* is most effective when using an MPV preparation in which gentamycin and nafcillin are incorporated into one liposome preparation.

7.1. Preparation of MPVs Containing Both Gentamycin and Nafcillin

A 10 ml ethanol solution of 100 mg EPC was prepared in a round bottom flask. The following two solutions were added to the lipid ethanol solution simultaneously: 100 mg gentamycin in 1.5 ml PBS and 100 mg nafcillin in 1.5 ml PBS. The resulting mixture (a dispersion) was evaporated at 54° C. for three minutes until a clear film formed on the side of the vessel. Then 10 ml of PBS was added and the mixture was agitated to form and resuspend the MPVs.

7.2. Treatment of Infected Mice

Sixty-five mice were infected by intraperitoneal (I.P.) inoculation of a lethal dose (i.e., $5 \times 10^6$ CFU) of *S. typhimurium* in order to establish septicemia. Twenty-four hours after inoculation the mice were divided into 3 groups and treated as follows: Group 1 (controls) received no treatment; Group 2 received a single preparation containing both aqueous gentamycin (100 mg/kg body weight) and aqueous nafcillin (100 mg/kg body weight, I.P.); Group 3 received one MPV preparation containing both gentamycin (100 mg/kg body weight, I.P.) and nafcillin (50 mg/kg body weight, I.P.) prepared as described in Section 6.2. Results are shown in Table III.

Results shown in Table IV clearly demonstrate that the MPVs containing gentamycin and nafcillin coencapsulated were most effective in preventing morality due to infection.

TABLE IV

| | EFFECT OF MPV-ENTRAPPED GENTAMYCIN AND NAFCILLIN | | | | | | | | |
|---|---|---|---|---|---|---|---|---|---|
| | SURVIVAL[b] DAYS AFTER INFECTION | | | | | | | | % |
| GROUP[a] | 1-2 | 3 | 4 | 5 | 6 | 7-10 | 11-12 | 13-15 | SURVIVAL |
| GROUP 1 CONTROL (untreated) | 20/20 | 5/20 | 2/20 | 0/20 | 0/20 | 0/20 | 0/20 | 0/20 | 0 |
| GROUP 2 GENT/NAF (aq.) | 20/20 | 15/20 | 10/20 | 6/20 | 1/20 | 0/20 | 0/20 | 0/20 | 0 |
| GROUP 3 MPV/ GENT-NAF | 25/25 | 25/25 | 25/25 | 25/25 | 25/25 | 25/25 | 24/25 | 23/25 | 92 |

[a]Each animal received a total of 100 mg antibiotic/kg body weight (except for the control group which received no treatment) 24 hours after infection with a lethal dose of *S. typhimurium* ($5 \times 10^6$ CFU, I.P.).
[b]Survival is expressed as the number of mice alive divided by the total number of mice in the group.

8. EXAMPLE: ENHANCEMENT OF ANTIBACTERIAL ACTIVITY IN TREATING *CORYNEBACTERIUM RENALE* PYELONEPHRITIS USING SPLVS CONTAINING GENTAMYCIN AND NAFCILLIN

In this example, the antibacterial activity and preparations of clinical effectiveness of various gentamycin and nafcillin are compared. The results indicate that of the preparations tested, treatment of *Corynebacterium renale* pyelonephritis is most effective when using an SPLV preparation in which gentamycin and nafcillin are both incorporated into one liposome preparation.

8.1 Preparation of SPLVS

The SPLVS containing either gentamycin or nafcillin were prepared as described in Section 5.1. The SPLVs containing both gentamycin and nafcillin were prepared as described in Section 5.2.

8.2 Infection of Mice Using *Corynebacterium Renale*

A *Corynebacterium renale* pyelonephritis was induced in adult Hilltop mice (20-30 gm each) essentially by the method of Snumono and Yanagawa (Infection and Immunity, Apr. 1977, pp. 263-267) as follows: each mouse was anesthetized using ether, the abdominal wall was incised and the bladder isolated. The bladder contents were evacuated by applying gentle pressure. A suspension of *C. renale* in BHI (BBL Microbiological Systems, Cockeysville, Md.) at a concentration of $10^7$ CFU (colony forming units) per ml was inoculated in to the bladder until full (approximately 0.1 to 0.2 ml per injection or $10^6$ organisms per mouse bladder). The abdominal wall was then closed. The *C. renale* had been prepared by growing *C. renale* ATCC strain No. 10848 overnight in BHI broth. Organisms were then suspended in saline to an $O.D._{420}$ of approximately 0.78. Ser. dilutions were plated on agar in order to determine the CFU per ml for each dilution.

8.3 Treatment of Infected Mice

Twenty four hours after inoculation with *C. renale* the mice were divided into 7 groups and each group was treated as follows: Group 1 (controls) received no treatment; Group 2 received aqueous gentamycin (100 mg/kg body weight, I.P.); Group 3 received SPLVs containing gentamycin (100 mg/kg body weight, I.P.); Group 4 received aqueous nafcillin (100 mg/kg body weight, I.P.); Group 5 received SPLVs containing nafcillin (100 mg/kg body weight, I.P.); Group 6 received a single aqueous preparation containing both gentamycin (100 mg/kg body weight, I.P.) and nafcillin (100 mg/kg body weight, I.P.); and Group 7 received one SPLV preparation containing both gentamycin (100 mg/kg body weight) and nafcillin (100 mg/kg body weight) I.P. Results are shown in Table V.

TABLE V

| | EFFECT OF SPLV ENTRAPPED GENTAMYCIN AND NAFCILLIN ON *C. RENALE* PYELONEPHRITIS IN MICE | | | | | | | |
|---|---|---|---|---|---|---|---|---|
| | SURVIVAL DAYS AFTER TREATMENT | | | | | | | % |
| GROUP[1] | 1 | 2 | 3 | 4 | 5 | 6 | 7 | SURVIVAL |
| GROUP 1 CONTROLS (untreated) | 15/15 | 15/15 | 7/15 | 1/15 | 1/15 | 0/15 | 0/15 | 0 |
| GROUP 2 GENTAMYCIN (100 mg/kg) | 10/10 | 10/10 | 4/10 | 1/10 | 1/10 | 1/10 | 1/10 | 10 |
| GROUP 3 SPLV-GENT (100 mg/kg) | 10/10 | 10/10 | 10/10 | 5/10 | 5/10 | 3/10 | 0/10 | 0 |
| GROUP 4 NAFCILLIN (100 mg/kg) | 10/10 | 10/10 | 7/10 | 0/10 | 0/10 | 0/10 | 0/10 | 0 |
| GROUP 5 SPLV-NAF (100 mg/kg) | 10/10 | 10/10 | 5/10 | 0/10 | 0/10 | 0/10 | 0/10 | 0 |
| GROUP 6 GENT/NAF (aq.) (100 mg/kg | 10/10 | 10/10 | 8/10 | 0/10 | 0/10 | 0/10 | 0/10 | 0 |

TABLE V-continued

EFFECT OF SPLV ENTRAPPED GENTAMYCIN AND
NAFCILLIN ON *C. RENALE* PYELONEPHRITIS IN MICE

| GROUP[1] | SURVIVAL DAYS AFTER TREATMENT | | | | | | | % SURVIVAL |
|---|---|---|---|---|---|---|---|---|
| | 1 | 2 | 3 | 4 | 5 | 6 | 7 | |
| each) | | | | | | | | |
| GROUP 7 SPLV-GENT/NAF (100 mg/kg each) | 10/10 | 10/10 | 10/10 | 10/10 | 10/10 | 10/10 | 10/10 | 100 |

[1] All mice were treated by intraperitoneal injection 24 hours after infection.

The results in Table V clearly indicate that the SPLVS containing both gentamycin and nafcillin were most effective in preventing mortality due to *C. renale* pyelonephritis.

In another set of experiments, the effectiveness of gentamycin and nafcillin entrapped in one SPLV preparation was also compared to the effectiveness of administering the two drugs separately contained in SPLVs. Accordingly, mice were infected with *C. renale* as described in Section 8.2. Twenty four hours after inoculation with *C. renale* the mice were divided into 4 groups and each group was treated as follows: Group 1 (control) received no treatment; Group 2 received aqueous nafcillin (100 mg/kg body weight, I.P.) followed by aqueous gentamycin (100 mg/kg body weight, I.P.) administered 1 hour after the nafcillin (NAF-GENT, aq.; N.B., the aqueous preparations of nafcillin and gentamycin were administered one hour apart in order to prevent in situ inactivation of the drugs); Group 3 received a mixture of two SPLV preparations, one containing gentamycin (SPLV-GENT; 100 mg/kg body weight) and the other SPLV preparation containing nafcillin (SPLV-NAF; 100 mg/kg body weight) I.P.; and Group 4 received one SPLV preparation (SPLV/GENT-NAF) containing both gentamycin (100 mg/kg body weight) and nafcillin (100 mg/kg body weight) I.P. The results shown in Table VI demonstrate that the SPLV/GENT-NAF preparation was the most effective in treating the infection.

The surviving mice which were treated with the SPLV preparation containing both gentamycin and nafcillin were sacrificed at day 14 and the right kidneys were tested for the presence of *C. renale* whereas the left kidneys were analyzed histologically.

The right kidneys were homogenized in BHI media. The homogenate was serially diluted and plated on agar. No growth of organisms was detected in cultures of the right kidneys of the 8 surviving mice. Histologic examination of the left kidney revealed no lesions in 5/8 of the kidneys sampled, minimal to moderate chronic inflammation in the lining of the pelvis of 2 mice, and purulent pyelonephritis with focal necrosis and acute purulent inflammatory reaction in the center left kidney of only 1 mouse. Thus, histologic and bacteriological cure was demonstrated in the surviving animals.

9. EXAMPLE: ENHANCEMENT OF ANTIBACTERIAL ACTIVITY IN TREATING *PSEUDOMONAS AERUGINOSA* PYELONEPHRITIS USING MPVs CONTAINING TOBRAMYCIN AND TICARCILLIN

In this example, the antibacterial activity and clinical effectiveness of various preparations of tobramycin (an aminoglycoside antibiotic) and ticarcillin (a β-lactam antibiotic) are compared. The results indicate that of the preparations tested, treatment of *Pseudomonas aeruginosa* pyelonephritis is most effective when using an MPV preparation in which tobramycin and ticarcillin are both incorporated into one liposome preparation.

9.1 Preparation of MPVs

MPVs containing both tobramycin and ticarcillin were prepared as follows: a 10 ml ethanol solution of 100 mg EPC was prepared in a round bottom flask. Then 100 mg ticarcillin in 1.5 ml PBS was added to the EPC ethanol solution to which 100 mg tobramycin in

TABLE VI

EFFECT OF SPLV ENTRAPPED GENTAMYCIN AND
NAFCILLIN ON *C. RENALE* PYELONEPHRITIS IN MICE

| GROUP | SURVIVAL DAYS AFTER TREATMENT[1] | | | | | | | % SURVIVAL |
|---|---|---|---|---|---|---|---|---|
| | 1 | 2 | 3 | 4 | 5 | 6–11 | 12–14 | |
| GROUP 1 CONTROLS | 7/8 | 2/8 | 1/8 | 0/8 | 0/8 | 0/8 | 0/8 | 0 |
| GROUP 2 NAF-GENT (aq.) | 10/10 | 10/10 | 1/10 | 0/10 | 0/10 | 0/10 | 0/10 | 0 |
| GROUP 3 SPLV-GENT & SPLV-NAF | 10/10 | 10/10 | 6/10 | 3/10 | 2/10 | 0/10 | 0/10 | 0 |
| GROUP 4 SPLV/ GENT-NAF | 9/10 | 9/10 | 9/10 | 9/10 | 9/10 | 9/10 | 8/10 | 80 |

0.5 ml PBS lacking divalent cations (PBS-) was added. The resulting mixture (a dispersion) was evaporated at 54° C. for 3 minutes until a film formed on the side of the vessel. Then 10 ml of PBS was added and the mixture was agitated to form and resuspend the MPVs.

MPVs containing either tobramycin or ticarcillin were prepared as described above except that 100 mg of either tobramycin or 100 mg of ticarcillin in PBS was added to the EPC ethanol solution.

9.2. Infection of Rats Using *Pseudomonas Aeruginosa*

Sprague Dawley rats (approximately 0.2 kg each) were infected with *P. aeruginosa* by the following technique: female rats were anesthetized using Brevital (10.64 mg/200 gm rat) administered subcutaneously. The urinary bladder was exposed by a midline incision made after shaving the abdomen. A small incision was made in the bladder and all urine was drained after which a zinc pellet (3 mm in diameter) was inserted into the bladder. The bladder incision was tied off using silk thread and a 0.1 ml inoculum of a *P. aeruginosa* culture which was grown overnight in TSB (Trypticase Soy Broth, BBL Microbiological Systems, Cockeysville, Md) was injected into the bladder. The abdominal incision was then closed.

9.3. Treatment of Infected Rats

Infected rats were divided into 5 groups which were treated with two doses of the following preparations administered intraperitoneally at 4 and 28 hours after inoculation with *P. aeruginosa:* Group 1 (controls) received no treatment; Group 2 received aqueous tobramycin (4 mg/kg body weight); Group 3 received MPVs containing tobramycin (4 mg/kg body weight); Group 4 received aqueous tobramycin (400 mg/kg body weight) and ticarcillin (4 mg/kg body weight); and Group 5 received one MPV preparation (MPV/TIC-TOBRA) containing both tobramycin (400 mg/kg body weight) and ticarcillin 4 mg/kg body weight).

The surviving rats were sacrificed at day 6 and each pair of kidneys was tested for the presence of *P. aeruginosa* as follows: after each kidney was removed, it was placed on a petri dish containing ethanol, flamed and then homogenized in 2 ml TSB. The homogenate was adjusted to a final volume of 10 ml using TSB. Serial 10-fold dilutions of the homogenate were plated in duplicate on agar, and the CFU/ml were determined for each pair of kidneys. Results are shown in Table VII.

was most effective in the treatment of *Pseudomonas pyelonephritis.*

10. EXAMPLE: ENHANCEMENT OF ANTIBACTERIAL ACTIVITY AGAINST *CLOSTRIDIUM NOVYI* USING SPLVS CONTAINING GENTAMYCIN AND CLINDAMYCIN

In this example, the antibacterial activity and clinical effectiveness of various preparations of gentamycin (an aminoglycoside antibiotic) and clindamycin (a derivative of the amino acid trans-L-4-n propylhygrinic acid attached to a sulfur-containing derivative of an octose) in the treatment of anaerobic would infection of Clostridium novyi.

10.1. Preparation of SPLVs

SPLVs containing gentamycin (SPLV/GENT) were prepared as described in Section 5.1 using 100 mg gentamycin. SPLVs containing clindamycin (SPLV/CLIN) were prepared the same way except that 100 mg clindamycin was used in place of the gentamycin. SPLVs containing both gentamycin and clindamycin in one liposome preparation (SPLV/GENT-CLIN) were prepared by the procedure described in Section 5.2 using 100 mg of each antibiotic, gentamycin and clindamycin. All SPLV preparations were washed three times in physiological saline.

10.2. Infection of Mice Using *Clostridium Novyi*

Twenty Swiss Webster adult female mice were injected in the right rear footpad with 0.05 ml of a suspension of *a Clostridium* novyi prepared as follows: *C. novyi* were grown for one day to stationary phase ($10^8$ to $10^9$ CFU/ml) in BHI media in an anaerobic blood bottle. The inoculum was prepared by diluting the culture 1:100 using fresh degassed BHI media; thus the inoculum contained approximately $10^7$ CFU/ml.

TABLE VII

EFFECT OF SPLV ENTRAPPED TOBRAMYCIN AND TICARCILLIN ON *P. AEROGINOSA* PYELONEPHRITIS IN RATS

| GROUP | SURVIVORS 6 DAYS POST INFECTION | $LOG_{10}$ CFU OF *P. AERUGINOSA* RECOVERED IN KIDNEY HOMOGENATE RAT | | | | | | |
|---|---|---|---|---|---|---|---|---|
| | | 1 | 2 | 3 | 4 | 5 | 6 | 7 |
| GROUP 1 CONTROL (no treatment) | 5/7 | 6 | 4 | 4 | 5 | 8 | ND | ND |
| GROUP 2 TOBRAMYCIN (aq.) (4 mg/kg) | 7/7 | 4 | 3 | 4 | 0 | 0 | 4 | 0 |
| GROUP 3 MPV-TOBRA (4 mg/kg) | 4/7 | 3 | 7 | 4 | 0 | ND | ND | ND |
| GROUP 4 TICARCILLIN TOBRAMYCIN (aq.) (4 mg/kg - 400 mg/kg) | 5/7 | 2 | 5 | 4 | 0. | 0 | ND | ND |
| GROUP 5 MPV/TIC-TOBRA (400 mg/kg - 4 mg/kg) | 7/7 | 0 | 0 | 0 | 0 | 0 | 4 | 0 |

These results indicate that the combination of tobramycin and ticarcillin contained in one MPV preparation

10.3. Treatment of Infected Mice

Twenty four hours after infection the mice were divided into 4 groups of 5 mice each which were treated as follows: Group 1 (controls) received no treatment; Group 2 received SPLVs containing gentamycin (100 mg gentamycin/kg body weight, I.P.); Group 3 received SPLVs containing clindamycin (100 mg clindamycin/kg body weight, I.P.); and Group 4 received SPLVs containing both clindamycin and gentamycin in one liposome preparation (100 mg of each antibiotic per kg body weight, I.P.). The diameters of the infected feet were measured using calipers and compared to control mice which were injected only with fresh media. Results are shown in Table VIII.

TABLE VIII

EFFECT OF SPLVS CONTAINING GENTAMYCIN AND CLINDAMYCIN ON *CLOSTRIDIUM NOVYI* INFECTION IN MICE

| GROUP | MEAN[1] FOOTPAD DIAMETER (INCHES) | SURVIVAL DAYS POST INFECTION | | | | | | % SURVIVAL |
|---|---|---|---|---|---|---|---|---|
| | | 1 | 2 | 3 | 4 | 5 | 6–19 | |
| GROUP 1 Control Untreated | 0.167 | 0/5 | 0/5 | 0/5 | 0/5 | 0/5 | 0/5 | 0 |
| GROUP 2 SPLV/GENT | 0.177 | 5/5 | 3/5 | 0/5 | 0/5 | 0/5 | 0/5 | 0 |
| GROUP 3 SPLV/CLIN | 0.177 | 5/5 | 1/5 | 1/5 | 0/5 | 0/5 | 0/5 | 0 |
| GROUP 4 SPLV/ GENT-CLIN | 0.166 | 5/5 | 4/5 | 4/5 | 4/5 | 4/5 | 3/5 | 60 |

[1]The mean footpad diameter of uninfected mice inoculated with fresh media is 0.119.

These results demonstrate that SPLVs containing both gentamycin and clindamycin in one liposome preparation were most effective in the treatment of the anerobic infection of the wounds.

It will be apparent to those skilled in the art that many modifications and variations may be made without departing from the spirit and scope of the invention. The specific embodiments described are given by way of example only and the invention is limited only by the appended claims.

What is claimed is:

1. A liposome-drug preparation comprising at least two antimicrobial drugs which are non-antagonistic as determined by the Combination Effect Test, Coencapsulated in lipid vesicles.

2. The liposome-drug preparation according to claim 1, in which said lipid vesicles are stable plurilamellar vesicles.

3. The liposome-drug preparation according to claim 1, in which said lipid vesicles are monophasic 4. The liposome-drug preparation according to claim 1, in which the antimicrobial drugs are synergistic in their unencapsulated form.

5. The liposome-drug preparation according to claim 1, in which the antimicrobial drugs demonstrate synergy in their unencapsulated form, synergy being determined by the Combination Effect Test.

6. The liposome-drug preparation according to claim 1, in which the antimicrobial drugs demonstrate addition in their unencapsulated form, addition being determined by the Combination Effect Test.

7. The liposome-drug preparation according to claim 1, in which the antimicrobial drugs demonstrate indifference in their unencapsulated form, indifference being determined by the Combination Effect Test.

8. A liposome-drug preparation comprising at least two antimicrobial drugs coencapsulated in lipid vesicles in which the therapeutic index of the liposome-drug preparation is greater than the therapeutic index of the combined antimicrobial drugs in their unencapsulated form.

9. The liposome-drug preparation according to claim 1 in which at least one antimicrobial drug is antibacterial.

10. The liposome-drug preparation according to claim 8 in which at least one antimicrobial drug is antibacterial.

11. The liposome-drug preparation according to claim 1 in which at least one antimicrobial drug is antifungal.

12. The liposome-drug preparation according to claim 8 in which at least one antimicrobial drug is antifungal.

13. The liposome-drug preparation according to claim 1 in which at least one antimicrobial drug is antiviral.

14. The liposome-drug preparation according to claim 8 in which at least one antimicrobial drug is antiviral.

15. The liposome-drug preparation according to claim 1, in which said antimicrobial drugs are an aminoglycoside antibiotic and a $\beta$-lactam antibiotic.

16. The liposome-drug preparation according to claim 15, in which the aminoglycoside antibiotic is gentamycin.

17. The liposome-drug preparation according to claim 15, in which the aminoglycoside antibiotic is tobramycin.

18. The liposome-drug preparation according to claim 15, in which the $\beta$-lactam antibiotic is nafcillin.

19. The liposome-drug preparation according to claim 15, in which the $\beta$-lactam antibiotic is nafcillin.

20. The liposome-drug preparation according to claim 15, in which the aminoglycoside antibiotic is gentamycin and the $\beta$-lactam antibiotic is nafcillin.

21. The liposome-drug preparation according to claim 15, in which the aminoglycoside antibiotic is tobramycin and the $\beta$-lactam antibiotic is ticarcillin.

22. The liposome-drug preparation according to claim 1 in which said antimicrobial agents are gentamycin and clindamycin.

23. The liposome-drug preparation according to claim 20, in which the lipid vesicles are stable plurilamellar vesicles.

24. The liposome-drug preparation according to claim 21, in which the lipid vesicles are stable plurilamellar vesicles.

25. The liposome-drug preparation according to claim 22, in which the lipid vesicles are stable plurilamellar vesicles.

26. The liposome-drug preparation according to claim 20, in which the lipid vesicles are monophasic vesicles.

27. The liposome-drug preparation according to claim 21, in which the lipid vesicles are monophasic vesicles.

28. The liposome-drug preparation according to claim 22, in which the lipid vesicles are monophasic vesicles.

29. A method for the treatment of an infection caused by a microbial agent comprising administering to the infected organism an effective amount of a liposome-drug preparation of claim 1.

30. The method according to claim 29, in which said administration is parenteral.

31. The method according to claim 29, in which said administration is topical.

32. The method according to claim 29, in which said administration is ocular.

33. A method for the treatment of an infection caused by a microbial agent comprising administering the infected organism a liposome-drug preparation of claim 4.

34. A method for the treatment of an infection caused by a microbial agent comprising administering the infected organism a liposome-drug preparation of claim 5.

35. A method for the treatment of an infection caused by a microbial agent comprising administering the infected organism a liposome-drug preparation of claim 6.

36. A method for the treatment of an infection caused by a microbial agent comprising administering to the infected organism a liposome-drug preparation of claim 7.

37. A method for the treatment of an infection caused by a microbial agent comprising administering to the infected organism a liposome-drug preparation of claim 8.

38. A method for the treatment of an infection caused by a microbial agent comprising administering the infected organism a liposome-drug preparation of claim 9 or 10.

39. A method for the treatment of an infection comprising administering to an organism the liposome-drug preparation of claim 23.

40. A method for the treatment of an infection comprising administering to an organism the liposome-drug preparation of claim 24.

41. A method for the treatment of an infection comprising administering to an organism the liposome-drug preparation of claim 25.

42. A method for the treatment of an infection comprising administering to an organism the liposome-drug preparation of claim 26.

43. A method for the treatment of an infection comprising administering to an organism the liposome-drug preparation of claim 27.

44. A method for the treatment of an infection comprising administering to an organism the liposome-drug preparation of claim 28.

45. The method according to claim 39 or 42, in which said infection is caused by Salmonella spp.

46. The method according to claim 45, in which said administration is parenteral.

47. The method according to claim 39 or 42, in which said infection is caused by Corynebacterium spp.

48. The method according to claim 47, in which said administration is parenteral.

49. The method according to claim 40 or 43, in which said infection is caused by Pseudomonas spp.

50. The method according to claim 49, in which said administration is parenteral.

51. The method according to claim 41 or 44, in which said infection is caused by Clostridium spp.

52. The method according to claim 51, in which said administration is parenteral.

* * * * *